United States Patent [19]

Soost et al.

[11] Plant 4,645

[45] Feb. 10, 1981

[54] GRAPEFRUIT HYBRID

[75] Inventors: Robert K. Soost; James W. Cameron, both of Riverside, Calif.

[73] Assignee: The Regents of the University of California, Berkeley, Calif.

[21] Appl. No.: 68,050

[22] Filed: Aug. 20, 1979

[51] Int. Cl.[3] ..... A01H 5/03

[52] U.S. Cl. ..... Plt./45

[58] Field of Search ..... Plt./45

*Primary Examiner*—Robert E. Bagwill

*Attorney, Agent, or Firm*—Townsend and Townsend

[57] ABSTRACT

A new and distinct variety of a grapefruit hybrid citrus tree characterized by early maturing habit when grown in the inland citrus areas of California and further characterized by its nearly seedless white-fleshed fruit lacking in bitterness. Fruit is tender and juicy and fruit flesh separates well from segment membranes.

2 Drawing Figures

This invention relates to a new and distinct variety of grapefruit hybrid plant characterized by early maturing habit when grown in the inland citrus areas of California such as Riverside and Lindcove where fruit matures several months earlier than present grapefruit cultivars. The variety is further characterized by its seedless white-fleshed fruit lacking in bitterness. Fruit is tender and juicy and fruit flesh separates well from segment membranes.

The variety of this invention is the result of a cross made in 1958 of an essentially acidless pummelo, CRC 2240 (*Citrus grandis* Osbeck), which had been shown to impart low acidity to its progenies was crossed as seed parent with a seedy, white, tetraploid grapefruit (*C. paradisi* Macf.). The cross was made in April 1958 and the trees field planted in 1962. The small population from this cross consisted of one tetraploid and six triploids. Two of the triploids had particularly favorable characteristics and were propagated for further testing. One of these, 6C26,20, the cultivar of this application, has been found suitable for release and is named Oroblanco. Observations have been made and data collected at Riverside since 1967. Additional test trees were planted at the University of California, Lindcove Field Station, South Coast Field Station and near Thermal in the Coachella Valley. Some fruit has been available for testing at these locations since 1972.

The variety of this invention has been asexually reproduced at Riverside, and the Lindcove and South Coast Field Stations by grafting on rootstocks of Troyer citrange, *Poncirus trifoliata* (L.) Raf., Rough lemon, Brazilian sour orange, Red rough lemon, citremon 1449, grapefruit, and sweet orange. Tree growth is vigorous on all stocks with no bud union abnormalities. Rough lemon and Red rough lemon have had adverse effects on interior physical characteristics and juice quality. Data is still insufficient for critical comparisons among rootstocks.

Figure 1:
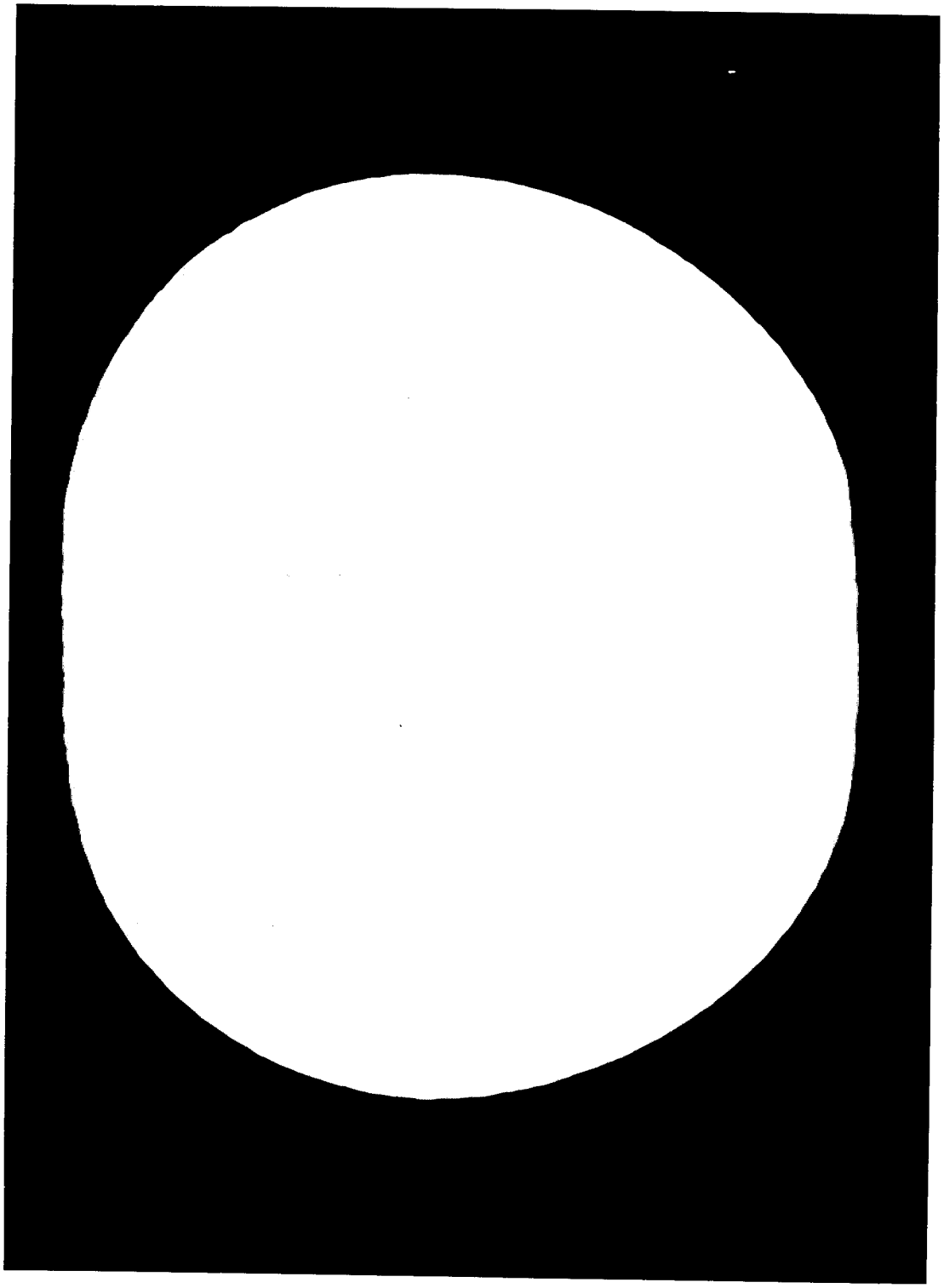
Figure 2:
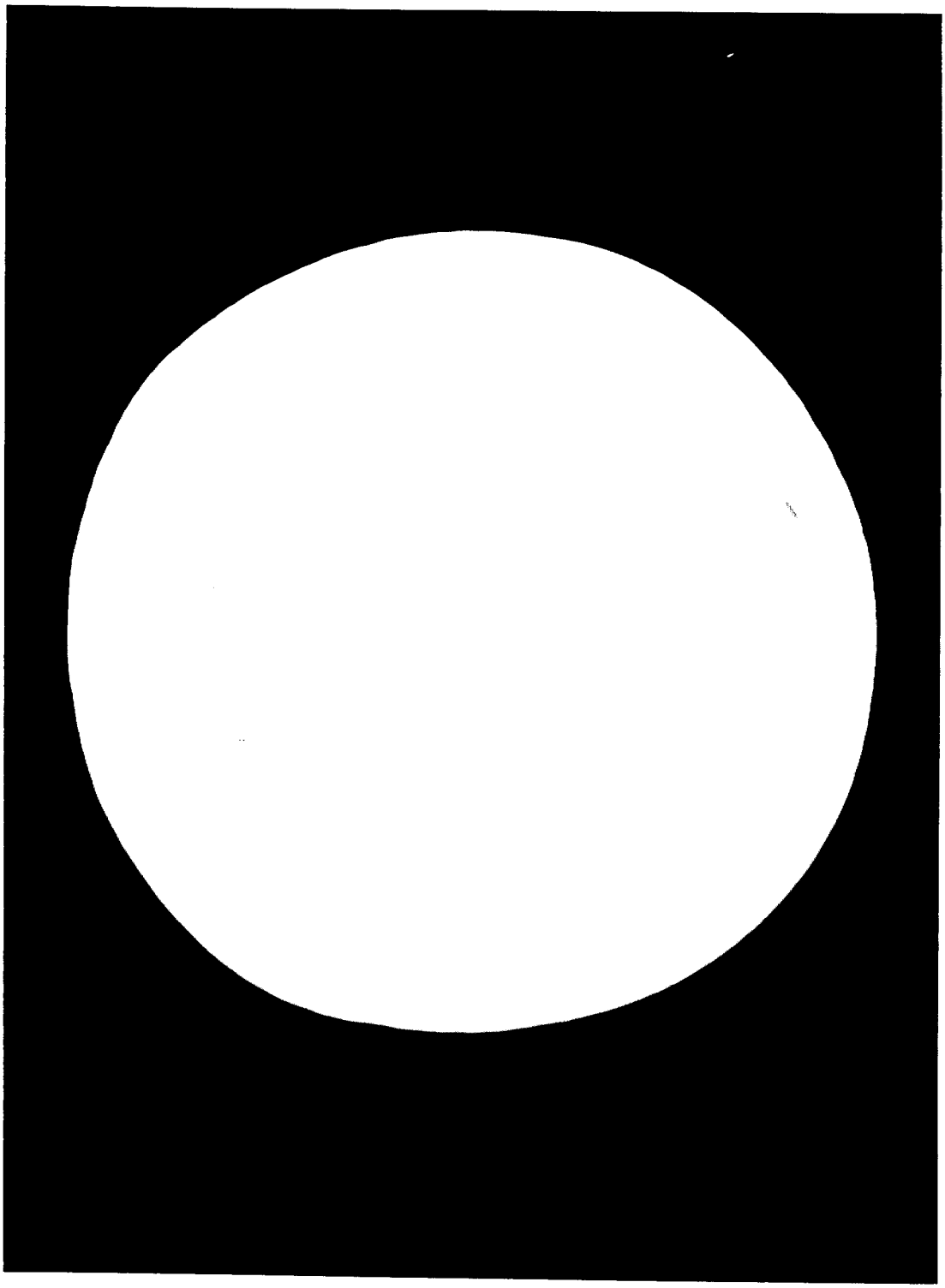

FIG. 1 of the accompanying drawings illustrates typical whole fruit of the new variety; and, FIG. 2 illustrates typical cut fruit of the new variety. variety.

The general characteristics of the fruit of Oroblanco are similar to those of present seedless, white-fleshed grapefruit cultivars. Fruit size and shape has been comparable to Marsh grapefruit at all test locations. Peel color is paler than Marsh at comparable dates. Exterior color is not well developed in fruit harvested in November at Lindcove. Peel thickness is greater than Marsh at all test locations. Other interior characteristics are very similar to Marsh. Oroblanco has slightly paler flesh and a larger hollow core. The flesh is tender and juicy, separating well from the segment membranes. It is slightly lower in percent juice than Marsh, probably because of its thicker rind.

Oroblanco lacks the bitterness of grapefruit, particularly grapefruit from cooler areas. An astringent aftertaste has been detected by some persons. This astringency is more noticeable early in the season and in cooler environments.

Table One below set forth, compares total soluble solids, percent titratable acid, and solids to acid ratios of Oroblanco and Marsh for December of the years of record at Riverside. The data for Oroblanco are from the original orchard tree except for the last two years. The levels of solids and acid are slightly higher than those obtained from younger trees in more recent plantings. The elevated levels are probably due to the crowded condition of the original plantings and the resulting slow growth. However, the ratios have been very similar.

TABLE ONE

Percentages of soluble solids and acid, and solids-to-acid ratios of OROBLANCO and MARSH at Riverside, California, in several years.[z]

| YEAR | % SOLUBLE SOLIDS OROBLANCO | MARSH | % ACID OROBLANCO | MARSH | SOLIDS:ACID RATIO OROBLANCO | MARSH |
|---|---|---|---|---|---|---|
| 1967 | 13.3 | 11.1* | 1.22 | 1.95* | 10.9 | 5.7* |
| 1969 | 12.9 | 11.6 | 1.20 | 2.07 | 10.8 | 5.6 |
| 1970 | 12.1 | 11.8* | 1.19 | 1.96* | 10.2 | 6.0* |
| 1971 | 13.7 | 10.4 | 1.61 | 2.02 | 8.5 | 5.1 |
| 1972 | 13.5 | 9.3 | 1.06 | 1.62 | 12.7 | 5.7 |
| 1973 | 14.0 | 10.6 | 1.40 | 2.25 | 10.0 | 4.7 |
| 1974 | 10.8* | 8.8 | 0.94* | 1.60 | 11.5* | 5.5 |
| 1975 | 12.3 | 9.9 | 1.24 | 2.22 | 9.9 | 4.5 |

[z]All samplings made in mid-to-late December, except those marked with an asterisk (*), which were from the following January.

TABLE TWO

Table Two, below, shows the comparison for the 1969–70 season and for a late test in 1968 of percentages of soluble solids and acid, and solids-to-acid ratios of OROBLANCO and MARSH during the 1969–70 season at Riverside, California.[z]

| DATE | % SOLUBLE SOLIDS OROBLANCO | % SOLUBLE SOLIDS MARSH | % ACID OROBLANCO | % ACID MARSH | SOLIDS:ACID RATIO OROBLANCO | SOLIDS:ACID RATIO MARSH |
|---|---|---|---|---|---|---|
| 12/22/69 | 12.9 | 11.6 | 1.20 | 2.07 | 10.8 | 5.6 |
| 1/19/70 | 13.1 | 10.5 | 1.19 | 1.85 | 11.0 | 5.7 |
| 2/10/70 | 12.3 | — | 1.22 | — | 10.1 | — |
| 2/27/70 | 12.1 | 10.3 | 1.17 | 1.73 | 10.3 | 6.0 |
| 3/19/70 | 11.9 | 10.4 | 1.08 | 1.90 | 11.0 | 5.5 |
| 4/22/68[y] | 12.3 | 10.7 | 0.98 | 2.16 | 12.5 | 5.0 |

[z]Samples of 10 fruit at each date, from the same tree.
[y]This sample taken in a previous season.

More recent comparisons show a similar pattern to that shown in Table Two, above, but the 1969–70 data are presented because more samplings were made. Coachella Valley fruit from trees planted in 1970 on vigorous rootstocks has had lower acids and solids levels resulting in questionable fruit quality. The trees are excessively vigorous and yields are low. Fruit quality may improve as the trees age and yields increase. At South Coast Field Station acidity has been high in relation to solids except very late (May) in the season. Although ratios are still higher than with Marsh, the fruit has not had acceptable quality. Astringency and off-flavor have been particularly noticeable.

On the basis of present data and observations, Oroblanco is best adapted to the inland citrus areas over California. It probably will not provide an early maturing grapefruit-type fruit for the desert areas although additional testing is needed. In inland areas it will provide a grapefruit-type fruit several months earlier than present grapefruit cultivars. The season of use at Riverside is from mid-December until April. At Lindcove, fruit is mature in early November with the season extending through February. Taste tests indicate consistent preference for Oroblanco over Marsh grown at Riverside and Lindcove. The thicker rind of Oroblanco is no doubt its most unfavorable characteristic.

Long-term yielding behavior is uncertain. Test trees at Riverside and Lindcove have had moderate to heavy yields. Heavy yields may alternate with moderate to lower yields. With heavy yields, fruit size is reduced but compares favorably with Marsh with comparable yields.

Tree: Vigorous, dense, slightly drooping branches, many short, fine thorns in leaf axils. Fruit is borne singly or in clusters, much inside fruit.

Leaves: Large (96×71 mm), thick, ovate; apex broad acuminate; base rounded; edges entire to irregularly crenate. Petioles winged (11×20 mm), entire to obscurely crenate. Mature leaves and twigs glaborous, upper surface glossy dark green, lower surface light green; young shoots, ovaries and very young fruit slightly pubescent.

Fruit: Slightly oblate to slightly obovoid with no neck; base depressed but smooth; stylar scar depressed. Average length 8–10 cm; average width 10–12 cm.; average weight 350 gm. Nearly seedless. Rind grained; oil glands small (less than 1 mm), slightly depressed to slightly raised, color darker than rind. Rind color light yellow, darkening as maturity progresses (Munsell 2.5 GY 8/6 to 5 Y 9/8). Rind thickness variable, 10–15 mm. Interior segments usually 13 to 16; segment membranes medium thickness. Pulp color very pale yellow (Munsell 5 Y 9/4 to 7.5 Y 9/4). Pulp vesicles medium, tender, variable shape, juicy. Aroma pleasant, grapefruit-like.

Season of use: San Joaquin Valley, November to February; Riverside, mid-December to April.

Solids and acid: Soluble solids 10 to 14 percent; percent acid, 1.50 to 0.90; solids:acid ratio, 9.0 to 13.0; ascorbic acid level similar to and not lower than present commercial grapefruit cultivars (30 to 40 mg per 100 ml). We claim:

1. The new and distinct variety of grapefruit hybrid plant herein described and illustrated and identified by the characteristics enumerated above.

* * * * *